(12) United States Patent
Bogsnes et al.

(10) Patent No.: US 7,396,903 B2
(45) Date of Patent: Jul. 8, 2008

(54) PROCESS FOR PREPARING INSULIN COMPOUNDS

(75) Inventors: Are Bogsnes, Nivå (DK); Ingun Christensen, Birkerød (DK); Per Balschmidt, Espergaerde (DK)

(73) Assignee: Novo Nordisk A/S, Bagsvaerd (DK)

( * ) Notice: Subject to any disclaimer, the term of this patent is extended or adjusted under 35 U.S.C. 154(b) by 266 days.

(21) Appl. No.: 10/299,183

(22) Filed: Nov. 19, 2002

(65) Prior Publication Data

US 2003/0143663 A1  Jul. 31, 2003

Related U.S. Application Data

(60) Provisional application No. 60/339,223, filed on Dec. 11, 2001.

(30) Foreign Application Priority Data

Nov. 19, 2001  (DK) .............................. 2001 01716

(51) Int. Cl.
*C07K 17/00* (2006.01)
*C07K 14/62* (2006.01)

(52) U.S. Cl. .................. 530/303; 530/333; 530/338
(58) Field of Classification Search ............... 514/3; 530/303, 345

See application file for complete search history.

(56) References Cited

U.S. PATENT DOCUMENTS

| | | | | |
|---|---|---|---|---|
| 4,343,898 | A | 8/1982 | Markussen | 435/71 |
| 4,579,820 | A | 4/1986 | Breddam et al. | 435/71 |
| 4,601,979 | A | 7/1986 | Andresen et al. | 435/70 |

FOREIGN PATENT DOCUMENTS

| | | |
|---|---|---|
| EP | 87238 | 8/1983 |
| EP | 0092829 | * 11/1983 |
| WO | 83/00504 | 2/1983 |

\* cited by examiner

*Primary Examiner*—Anish Gupta
(74) *Attorney, Agent, or Firm*—Shelby J. Walker

(57) ABSTRACT

A preferred way of converting insulin precursors into insulin compounds is to perform an enzymatic peptide cleavage in an aqueous medium and, thereafter, without removal of the intermediate product formed, to add an amino acid ester or a peptide ester and an organic solvent so that the desired coupling takes place.

45 Claims, No Drawings

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Sequence determined by structural factors
```

```
<400> SEQUENCE: 1

Glu Glu Ala Glu Ala Glu Ala Pro Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Sequence determined by structural factors

<400> SEQUENCE: 2

Glu Glu Gly Glu Pro Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Sequence determined by structural factors

<400> SEQUENCE: 3

Gly Phe Phe Tyr Thr Lys Pro Thr
1               5
```

US 7,396,903 B2

PROCESS FOR PREPARING INSULIN COMPOUNDS

CROSS-REFERENCE TO RELATED APPLICATIONS

This application claims the benefit under 35 U.S.C. 119 of U.S. Ser. No. 60/339,223, filed Dec. 11, 2001 and of Danish application PA 2001 01716, filed Nov. 19, 2001, the contents of both of which are hereby incorporated by reference.

FIELD OF THE INVENTION

The present invention relates to an improved process for converting an insulin precursor into an insulin compound, optionally via an insulin ester.

BACKGROUND OF THE INVENTION

Insulin is a pancreatic hormone involved in the regulation of blood-glucose concentrations. For example, human, porcine, and bovine insulin, insulin analogues and mixed insulins are given to patients with insulin-dependent diabetes mellitus to control their blood-glucose concentrations.

Porcine and bovine insulin are, usually, prepared from pancreas glands. Human insulin can, semisynthetically, be prepared from porcine insulin. Alternatively, human insulin, as well as many insulin analogues, can be prepared by genetic engineering. By genetic engineering, which may, for example, be performed in bacteria or in yeast, an insulin precursor is prepared which, thereafter, is to be converted into the desired product. This conversion can be performed in different ways.

One possibility is the so-called transpeptidation where a peptide cleavage and a peptide coupling takes place consecutively in the same reaction mixture, under the same reaction conditions, vide, for example, U.S. Pat. No. 4,343,898 (Novo Industri).

Another possibility is, in the first step, to cleave the insulin precursor, vide, for example, *Hoppe-Seyler's Z Physiol. Chem.* 359 (1978), 799, thereafter, to isolate the intermediate product and, then, to perform the desired coupling in another reaction mixture than that used in the first step, vide, for example, *Nature* 280 (1979), 412.

According to EP 87,238, a transpeptidation reaction is performed in a solvent system comprising between about 75% and 97% (vol/vol) of at least one non-aqueous reaction miscible solvent including at least about 50% (vol/vol) butane-1,4-diol.

According to U.S. Pat. No. 4,579,820, the transpeptidation process is performed using an L-specific serine carboxypeptidase enzyme, for example carboxypeptidase Y.

According to U.S. Pat. No. 4,601,979 (Nordisk Insulinlaboratorium), the transpeptidation or only the peptide coupling is performed in an aqueous reaction medium substantially free of organic solvent.

According to WO 83/00504 (Nordisk Insulinlaboratorium), a porcine product was treated with carboxypeptidase A, the resulting des-alanine-B 30 insulin product was suspended in a lower alcohol, and this suspension was mixed with a solution of an L-threonine ester and trypsin. In all the specific examples, the des-alanine-B30 insulin product was isolated, either by freeze-drying or by precipitation.

SUMMARY OF THE INVENTION

The present invention relates to a process for preparing insulin compounds. These insulin compounds can be used as medicaments. In a preferred embodiment of this invention, insulin compounds having threonine (Thr) in the C terminal end of the B chain are prepared.

Any skilled art worker, for example, a physician, is able to determine which dosages of the insulin compounds to administer to a diabetic patient, and when.

The starting material for the process of this invention is an insulin precursor which is subjected to both a peptide cleavage and a peptide coupling at conditions favoring both reactions but where no isolation of the intermediate product takes place. In other words, the insulin precursor is subjected to a peptide cleavage and the resulting product, i.e., the intermediate, is subjected to a peptide coupling. The conditions favoring a peptide cleavage are not identical with the conditions favoring a peptide coupling. Hence, in the first step of this invention, i.e., the cleavage step or the cleavage reaction, the reaction conditions in the reaction mixture are chosen so as to favor the peptide cleavage and, in the second step of this invention, i e., the coupling step or the coupling reaction, the reaction conditions in the reaction mixture are altered so as to favor the peptide coupling.

In one embodiment of this invention, the insulin precursor is, in the first step, dissolved in a predominantly aqueous medium and the enzyme used for cleavage is added This reaction mixture may be free or substantially free of organic solvent. Alternatively, the reaction mixture may contain a certain amount of organic solvent which may ensure a proper solubility of the insulin precursor. However, it is desired not to use so much organic solvent that it has an undesired influence on the enzymatic cleavage. In the first step of the process of this invention, the reaction parameters such a pH value, temperature, and time, are chosen so that they are favorable to cleavage at the lysine residue(s) or arginine residue(s).

When the cleavage reaction has taken place to a certain, desired degree, a nucleophile compound and an organic solvent is mixed with the reaction mixture (without previous isolation of the intermediate product), so that the coupling of the nucleophile compound to the lysine or arginine residue of the desired intermediate product takes place. In this step, the reaction parameters are set so as to be favorable to the coupling reaction. In a preferred embodiment of this invention, the nucleophile compound is an amino acid ester, for example a threonine ester, or a peptide ester.

Thereafter, the protecting group(s) may, if desired, be removed from the resulting compound.

Accordingly, in one embodiment, this invention relates to a process for preparing an insulin compound wherein a) in a reaction mixture containing at least about 55%, preferably at least about 60%, more preferred at least 70%, water (weight/weight), an insulin precursor is subjected to an enzymatic cleavage and, thereafter, without isolation of the intermediate product from the reaction mixture, b) said intermediate product is coupled with a nucleophile compound in a reaction mixture having a content of water in the range from about 10% to about 50% water (weight/weight), preferably in the range from about 20% to about 40% water (weight/weight), and c), if desired, removing the protecting group(s).

In an alternative embodiment, the invention relates to a process for preparing an insulin compound wherein a) in a reaction mixture containing at least about 55%, preferably at least about 60%, more preferred at least 70%, water (weight/weight), an insulin precursor is subjected to an enzymatic cleavage and, thereafter, b) the intermediate product is coupled with a nucleophile compound in the reaction mixture used for the enzymatic cleavage reaction with the proviso that the composition of the reaction mixture has been modified so that the content of water in the reaction mixture is in the range from about 10% to about 50% water (weight/weight), preferably in the range from about 20% to about 40% water (weight/weight), and c), if desired, removing the protecting group(s).

In yet another embodiment, the above process may be carried out with no isolation of the intermediate product being performed between the cleavage step and the coupling step.

Compared with the known transpeptidation reaction, the advantages obtained by the process of this invention is a shorter, over all reaction time with the same amount of enzyme and a similar or higher yield. Compared with a two pot reaction with cleavage in an aqueous medium, isolation of the intermediate product, and coupling in a mixture of organic solvent and water, the advantages obtained by the process of this invention is a shorter, over all reaction time, the use of a lower amount of enzyme, and an easier process flow.

BRIEF DESCRIPTION OF THE FIGURES

SEQ ID NO.: 1 is the peptide moiety Glu-(Glu-Ala)$_3$-Pro-Lys-; SEQ ID NO.: 2 is the peptide moiety Glu-Glu-Gly-Glu-Pro-Lys-; and SEQ ID NO.: 3 is the peptide moiety Gly-Phe-Phe-Tyr-Thr-Lys-Pro-Thr.

DEFINITIONS

The term "amino acid" as used herein, refers to amino acids which can be coded for by nucleotide sequences. Analogously, this applies to the term amino acid residue which is an amino acid from which hydroxy has been removed from a carboxy group and/or hydrogen has been removed from an amino group.

Similarly, the terms peptide and peptide residue consists of amino acid residues Preferably, the peptide contains not more than 10 amino acid residues.

The term amino acid amide, as used herein, refers to an amino acid having an optionally substituted C terminal carboxamide group.

The term peptide amide, as used herein, refers to a peptide having an optionally substituted C terminal carboxamide group.

The term "insulin precursor", as used herein, refers to a polypeptide consisting of two peptide chains (corresponding to the A and B chains of insulin and, hereinafter, designated the A and B chains) which, similarly with insulin, are connected with each other via two disulphide bridges (from one cysteine (Cys) residue to another cysteine residue) between the two peptide chains and wherein, like in insulin, there is an disulphide bridge from one cysteine residue in the A chain to another cysteine residue in the A chain. In this insulin precursor there is, at least, one lysine or arginine residue in the B chain. Optionally, in this insulin precursor, the A and B chains are connected with each other via a third peptide chain (corresponding to the connecting peptide in insulin) between the C terminal end of the B chain and the N terminal end of the A chain. In case the A and B chains are connected with each other via this third peptide chain, lysine is present at the C terminal end of this third peptide. Optionally, in this insulin precursor, a fourth peptide chain may be connected to the N terminal end of the B chain. In case this fourth peptide chain is connected to the N terminal end of the B chain, lysine is present at the C terminal end of this fourth peptide chain. Furthermore, in this insulin precursor, there is an identity of the amino acid residues of at least 80%, preferably at least 85%, more preferred at lest 90%, and even more preferred at least 95%, compared with human insulin, with the proviso that the third and fourth peptide chains are to be disregarded for this calculation. In human insulin, there are disulphide bridges between $Cys^{A6}$ and $Cys^{A11}$, between $Cys^{A7}$ and $Cys^{B7}$, and between $Cys^{A20}$ and $Cys^{B19}$ and there is lysine in the B29 position.

The term "amino acid ester", as used herein, refers to an amino acid carrying a C terminal carboxy protecting group and, optionally, a hydroxy protecting group.

The term "peptide ester", as used herein, refers to a peptide wherein at least the C terminal carboxy group carries a carboxy protecting group. Optionally, any hydroxy group is protected and, optionally, the ε-amino group of any lysine residues is derivatised, preferably with a hydrophobic group, for example an acyl group having at least 10 carbon atoms. Preferably, the peptide ester contains not more than 10 amino acid residues.

The term nucleophile compound, as used herein, refers an amino acid ester, an amino acid amide, a peptide, a peptide ester, and a peptide amide. In any of these amino acid esters, amino acid amides, peptides, peptide esters, and peptide amides, the amino group in any lysine group is, optionally, derivatised, preferably with a hydrophobic group, for example, an acyl group having at least 10 carbon atoms.

The term "insulin compound", as used herein, refers to insulin from any species such as porcine insulin, bovine insulin, and human insulin and salts thereof such as zinc salts, and protamin salts. Furthermore, the term "insulin compound", as used herein, refers to what could briefly be designated "insulin analogues". Insulin analogues, as used herein, refers to insulin compounds wherein one or more of the amino acid residues have been exchanged with another amino acid residue and/or from which one or more amino acid residue has been deleted and/or from which one or more amino acid residue has been added, provided that said insulin analogue has a sufficient insulin activity. Examples of insulin analogues are described in the following patents and equivalents thereto: U.S. Pat. No. 5,618,913; EP 254,516; EP 280,534; U.S. Pat. Nos. 5,750,497; and 6,011,007. Examples of specific insulin analogues are insulin aspart (i.e., $[Asp^{B28}]$ human insulin), insulin lispro (i.e., $[Lys^{B28},Pro^{B29}]$ human insulin), and insulin glargin (i.e., $[Gly^{A21},Arg^{B31},Arg^{B32}]$ human insulin). The term "insulin analogue", as used herein also covers what could be designated insulin derivatives, i.e., compounds which a skilled art worker would generally considers derivatives of insulin, vide general textbooks, for example, insulin having a substituent not present in the parent insulin molecule.

Examples of insulin derivatives are insulins or insulin analogues having an optionally substituted carboxamide group. Also compounds which can be considered being both an insulin derivative and an insulin analogue are herein covered by the term insulin analogue. Examples of such compounds are described in the following patents and equivalents thereto: U.S. Pat. Nos. 5,750,497 and 6,011,007. Hence, a further example of a specific insulin analogue is insulin detemir (i.e., des-$Thr^{B30}$ human insulin γ $Lys^{B29}$ tetradecanoyl). The insulin compounds prepared by this invention have an anti-diabetic activity sufficiently high to be used to treat diabetic patients. The anti-diabetic activity can be determined using the so-called free fat cell assay.

The term pH value, as used herein, refers to the value measured with a pH meter by immersing a calomel combination glass electrode connected to the pH meter directly in the solution, the pH value of which is to be measured. The pH meter is calibrated with an aqueous standard buffer.

DETAILED DESCRIPTION OF THE INVENTION

As appears from claim 1, first a peptide cleavage takes place and, thereafter, a coupling reaction takes place.

Briefly, the Cleavage Reaction (i.e., the Enzymatic Cleavage) is Performed as Follows:

The enzymatic cleavage of the insulin precursor (i.e., the peptide cleavage) takes place in a reaction mixture containing at least about 55%, preferably at least about 60%, more preferred at least 70%, water (weight/weight).

In a preferred embodiment of this invention, the concentration of the insulin precursor in the reaction mixture wherein the enzymatic cleavage takes place is at least 2%, preferably in the range from about 5 to about 10% (weight/vol).

The cleavage reaction is performed in a neutral or alkaline medium, preferably having a pH value in the range from about 6 to about 11, more preferred in the range from about 8 to about 10.

In a preferred embodiment of this invention the amounts of enzyme compared with the amount of insulin precursor is in the range from approximately 0.05 to approximately 5% (weight/weight), preferably from approximately 0.1 to approximately 2%.

The tryptic enzyme is not material to practice of this invention. Trypsin is a well-characterized enzyme available in high purity, notably from bovine or porcine origin. From microbial origin, *Acromobacter lyticus* protease I (hereinafter designated ALP) can be obtained. Moreover, the enzyme form, whether it is a native enzyme or an active immobilized enzyme or an enzyme derivative, is not material to practice of this invention. If it is desired to split at the C terminal end of arginine, trypsin can be used and if it is desired to split at the C terminal end of lysine, either trypsin or ALP can be used. For the splitting at the C terminal end of lysine, ALP is preferred.

As examples of active enzyme derivatives can be mentioned acetylated trypsin, succinylated trypsin, glutaraldehyde treated trypsin, and immobilized trypsin or ALP derivatives.

If an immobilized trypsin or ALP is used, it is suspended in the reaction mixture or may be packed into a column.

To a great extent, the action of the enzyme is controlled by an interrelation of water and solvent content, the pH value, and the reaction temperature. Increasing the concentration of organic solvent in the reaction mixture and lowering of the pH value to around neutral shifts the usual enzymatic reaction from cleavage towards coupling. Reducing the temperature reduces the reaction rate, but might also reduce biproduct formation and enzyme denaturation.

In a preferred embodiment of this invention, the insulin precursor is dissolved in an aqueous medium having a concentration of acetate ions in the range from about 5 mM to about 500 mM, preferably in the range from about 20 mM to about 200 mM. For example, sodium, potassium, ammonium acetate or triethyl ammonium acetate can be used.

According to one embodiment of this invention, the insulin precursor (being a peptide) can be illustrated by the following general formula I:

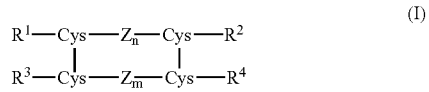

wherein $Z_n$ and $Z_m$, independent of each other, represents two peptide moieties each containing n and m amino acid residues, respectively, $R^1$ represents a peptide residue which peptide residue optionally contains a lysine or arginine residue, $R^2$ represents an amino acid residue or a peptide residue, $R^3$ represents a peptide residue which peptide residue optionally contains a lysine or arginine residue, $R^4$ represents a lysine or arginine residue or a peptide residue which peptide residue contains a lysine or arginine residue, or $R^1$ and $R^4$ are together a peptide residue containing a lysine or arginine residue, the two vertical lines indicate the disulphide bonds between the two cysteine residues and, furthermore, there is an disulphide bond between two cysteine residues present in $R^1$ and in $Z_n$.

Preferably, the amino acid residues present in the insulin precursor of formula I are those which can be coded for by the nucleotide sequences.

According to a preferred embodiment of this invention, an insulin precursor, wherein the number of amino acid residues in $R^1$ and $R^4$ together is in the range from about 8 to about 50, is used. In another preferred embodiment of this invention, $Z_n$ contains 12 amino acid residues. In another preferred embodiment of this invention, $Z_m$ contains 11 amino acid residues. In another preferred embodiment of this invention, $R^2$ contains 1 amino acid residue, for example, Asn or Gly. In another preferred embodiment of this invention, $R^3$ contains 6 amino acid residues.

In a preferred embodiment of this invention, the insulin precursor is a single chain precursor, i.e. a compound of formula I wherein $R^1$ and $R^4$ together are a peptide residue containing a lysine or arginine residue. Hence, preferably, the insulin precursor is not mammalian insulin such as porcine insulin, rabbit insulin, dog insulin or whale insulin According to another embodiment of this invention, the insulin precursor of formula I contains the same amino acid residues in positions A1 through A21 and in positions B1 through B29 as are present in human insulin in the same positions.

According to another embodiment of this invention, the insulin precursor of formula I contains the same amino acid residues in positions A1 through A21 and in positions B1 through B29 with the proviso that the B28 amino acid residue is Asp.

According to another embodiment of this invention, the insulin precursor of formula I contains the same amino acid residues in positions A1 through A21 and in positions B1 through B29 as are present in human insulin in the same positions with the proviso that the B28 amino acid residue is Lys and the B29 amino acid residue is Pro.

According to another embodiment of this invention, the insulin precursor of formula I contains the same amino acid residues in positions A1 through A21 and in positions B1 through B29 as are present in human insulin in the same positions with the proviso that the A21 amino acid residue is Gly and the B31 and B32 amino cid residues both are Arg Examples of specific insulin precursors which can be use in the process of this invention are human proinsulin; monkey proinsulin; [Ala³¹,Lys³²]-des(33-63) porcine proinsulin; porcine insulin; [Asp²⁸]-des(30-65) human proinsulin being N-terminally extended with Glu-(Glu-Ala)₃-Pro-Lys- (SEQ ID NO.: 1); and [Asp$^{28}$,Met$^{30}$,Trp$^{31}$,Lys$^{32}$]-des(33-65), human proinsulin being N-terminally extended with Glu-Glu-Gly-Glu-Pro-Lys- (SEQ ID NO.: 2).

The insulin precursors of formula I can be prepared as described in or analogously as described in the International applications having publication numbers WO 01/49742, WO 01/49870, WO 01/079250, and WO 02/079254, the content of which is hereby incorporated by reference.

The desired intermediate product (i.e., the desired cleavage product) corresponds to the insulin precursor wherein at least one lysine or arginine residue has been cleaved to form a lysyl or arginyl moiety, respectively. Furthermore, in the desired intermediate product, the A and B chains which are connected with each other via two disulphide bridges are not connected with each other via a peptide chain between the C terminal end of the B chain and the N terminal end of the A chain. In a preferred embodiment of this invention, the number of amino acid residues present in the desired intermediate product is in the range from about 48 to about 52, preferably in the range from about 49 to about 51, even more preferred 50. In another preferred embodiment of this invention, there are not more than 4, preferably not more than 3, more preferred not more than 2, and even more preferred not more than 1, of the amino acid residues present in the desired intermediate product which are not present at the corresponding position in human insulin.

According to one embodiment of this invention, the desired intermediate product (the desired cleavage product) can be illustrated by the general formula II

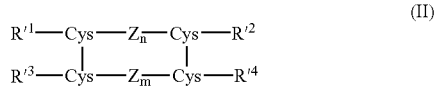

wherein $Z_n$ and $Z_m$, independent of each other, represents two peptide moieties each containing n and m amino acid residues, respectively, $R'^1$ represents a peptide residue, $R'^2$ represents an amino acid residue or a peptide residue, $R'^3$ represents a peptide residue, $R'^4$ represents lysine or arginine or a peptide residue containing a lysine or arginine residue in the C terminal end, the two vertical lines indicate the disulphide bond between the two cysteine residues and, furthermore, there is an disulphide bond between two cysteine residues present in $R'^1$ and in $Z_n$.

In a preferred embodiment of this invention, $R'^1$ is the amino acid residues A1 through A6 in human insulin in this order in which, optionally, one or two of the amino acid residues have been exchanged with another amino acid residue or wherein one or two of the amino acid residues are not present. In another preferred embodiment of this invention, $R'^2$ is -Asn or -Gly. In another preferred embodiment of this invention, $R'^3$ is the amino acid residues B1 through B6 in human insulin in this order in which, optionally, one or two of the amino acid residues have been exchanged with another amino acid residue or wherein one or two of the amino acid residues are not present. In another preferred embodiment of this invention, $R'^4$ is the amino acid residues B20 through B29 in human insulin in this order, the amino acid residues B20 through B29 in human insulin in this order with the proviso that it has Asp in B28, and the amino acid residues B20 through B28 in human insulin in this order with the proviso that it has Lys in B28, in each of which, optionally, one or two of the amino acid residues have been exchanged with another amino acid residue or wherein one or two of the amino acid residues are not present or a part of any of these peptide residues leaving out one or more consecutive amino acid residues from the C terminal end thereof. In another preferred embodiment of this invention, $Z_n$ is the amino acid residues A8 through A19 in human insulin in this order in which, optionally, one or two of the amino acid residues have been exchanged with another amino acid residue or wherein one or two of the amino acid residues are not present. In another preferred embodiment of this invention, $Z_m$ is the amino acid residues B8 through B18 in human insulin in this order in which, optionally, one or two of the amino acid residues have been exchanged with another amino acid residue or wherein one or two of the amino acid residues are not present.

During both the cleavage reaction and the coupling reaction, the reaction temperature is in the range from the freezing point of the reaction mixture to about 50° C. The preferred temperature is in the range from about 0° C. to about 25° C.

Briefly, the Coupling Reaction is Performed as Follows:

When at least about 25%, preferably at least 50%, more preferred at least 75%, preferably at least 85%, more preferred at least 95%, of the insulin precursor has been cleaved to the desired intermediate product, on one hand, the nucleophile compound and, on the other hand, organic solvent is mixed with the reaction mixture in which the cleavage took place so as to obtain reaction conditions which are convenient or favorable to the coupling step. The percentage of cleavage (conversion) is based upon the equilibrium possible in the reaction mixture used for cleavage. Usually, from the beginning of the enzymatic cleavage reaction and until a certain period of time has lapsed, the yield of the desired intermediate product, i.e., the desired cleavage product, increases and reaches a maximum concentration. Thereafter, the concentration of the desired cleavage product may decrease.

In a preferred embodiment of this invention, no components are removed from the reaction mixture resulting from the cleavage reaction before the coupling reaction takes place. A simple way of doing this is, after the cleavage reaction, to add the nucleophile compound and a sufficient amount of organic solvent. In this way, for example, the enzyme used in the cleavage step is also used in the coupling step.

The process of this invention also covers coupling reactions in a reaction mixture which besides the desired intermediate product contains a small amount of partially cleaved insulin precursor and/or unreacted insulin precursor.

In another preferred embodiment of this invention, the nucleophile compound is an amino acid amide or a peptide amide wherein the carboxamide group isn't substituted or is mono or disubstituted with an alkyl group with not more than 16 carbon atoms which alkyl group(s), together with the adjacent nitrogen atom, may form a ring or the carboxamide group is mono or disubstituted with an aryl group. The aliphatic substituents are preferred. Examples of substituted carboxamide groups are N,N-dimethylcarboxamide, N,N-diethylcarboxamide, and N-hexylcarboxamide.

In a preferred embodiment of this invention, the nucleo compound is an amino acid ester wherein the carboxyl group is protected and any hydroxy group optionally is protected. In a further preferred embodiment of this invention, the nucleo compound is a threonine ester wherein the carboxyl group is protected and, optionally, the hydroxy group is protected. Hence, an L-threonine ester can be illustrated by the following general formula IIIa:

wherein $R^6$ represents a carboxyl protecting group, and $R^5$ represents hydrogen or a hydroxyl protecting group. To make it more clear, a threonine ester can be illustrated by the general formula $CH_3$—$CH(OR^5)$—$CH(NH_2)COOR^6$, wherein $R^6$ and $R^5$ are as mentioned above.

Some nucleophile compounds are known compounds and the remaining nucleophile compounds can be prepared in analogy with the preparation of known compounds or in analogy with known methods.

The nucleophile compounds may be employed in the form of the free base or soluble salts thereof such as hydrochlorides, acetates, propionates, and butyrates.

When the coupling reaction starts, it is desirable that a substantial excess of nucleophile compound is present in the coupling reaction mixture solution, with the molar ratio between the nucleophile compound and the desired intermediate product preferably exceeding about 5:1. When the coupling reaction starts, the concentration of the nucleophile compound in the reaction mixture should preferably exceed 0.1 molar, the upper concentration limit being the solubility thereof.

To obtain a 60% yield considered herein as an important aspect to practice of this invention, the reaction temperature, water content and pH value are interrelated within the described ranges.

The organic solvents suited to practice of this invention are polar solvents which are miscible with water and preferably such that are capable of containing therein high concentrations of the desired intermediate product (for example of formula II) and the nucleophile compound. Examples of suitable organic solvents are aprotic solvents, such as N,N-dimethylformamide, N,N-dimethylacetamide, N-methylpyrrolidone-2, and dimethyl sulfoxide, and protic solvents, such as acetic acid, ethanol, methanol, 2-propanol, 1-propanol, butanol and 1,4-butanediol. Dioxane, acetone, tetrahydrofuran, formamide, and acetonitrile may also be used and even an amino acid ester used as the nucleophile compound can, fully or partially, be used as the organic solvent. The nature of the solvent does affect the system as a whole, and interrelationships suited to one solvent productive of high yields may not apply with a different solvent. Best yield results have been obtained with aprotic solvents, and aprotic solvents are most preferred for practice of this invention.

Obviously, when calculating or determining the content of water in the reaction mixture, the nucleophile compound is considered an organic solvent.

The addition of an acid, such as hydrochloric acid, formic acid, acetic acid, propionic acid, or butyric acid, or of a base, such as pyridine, TRIS, N-methylmorpholine, triethylamine, or N-ethylmorpholine, is optional. They are included in the reaction mixture to bring about a suitable pH value. Although mineral acids or bases may be used in practice of this invention, organic acids and bases are preferred, particularly those identified above. Organic acids are most preferred.

When the coupling reaction starts, the weight ratio between trypsin or ALP (calculated as crystalline trypsin or ALP or an amount of trypsin or ALP derivative corresponding thereto) and the desired intermediate product in the reaction mixture is preferably in the range from about 1:1000 to about 1:10, more preferred in the range from about 1:200 to about 1:50.

In some cases, the enzyme added in the cleavage step is sufficient for performing the coupling reaction and, in such case, there is no need for adding a further amount of enzyme during the coupling step. In other cases, it may be desirable to add an additional amount of enzyme during the coupling step.

Inasmuch as high concentrations of the desired intermediate product and of nucleophile compound in solution promote high conversion rates, solvent selection is biased towards those solvents in which the reactants are very soluble. The solubility of the nucleophile compound in particular is important, because that reactant should be present in high concentration. When the coupling reaction starts, the molar ratio of the nucleophile compound to the desired intermediate product should preferably exceed 5:1, preferably exceed 50:1. When the coupling reaction starts, the concentration of the nucleophile compound in the reaction mixture should preferably be at least 0.1 molar.

In a preferred embodiment of this invention, a nucleophile compound having carboxy protecting group(s) which can be removed from the resulting insulin compound under conditions, which do not cause substantial irreversible alterations in the insulin molecule, is used. As examples of such carboxyl protecting groups can be mentioned lower alkyl, for example, methyl, ethyl, and tert-butyl, substituted benzyl groups such as p-methoxybenzyl, diphenylmethyl, and 2,4,6-trimethylbenzyl, and groups of the general formula —$CH_2$—$CH_2$—$SO_2R^7$, wherein $R^7$ represents lower alkyl, such as methyl, ethyl, propyl, and n-butyl.

Suitable hydroxyl protecting groups are those which can be removed under conditions which do not cause substantial irreversible alteration in the insulin molecule. As an example of such a group can be mentioned tert-butyl.

Further protection groups usually used are described by Wunch: Metoden der Organischen Chemie (Houben-Weyl), Vol. XV/1, editor: Eugen Muller, Georg Thieme Verlag, Stuttgart 1974.

According to one embodiment of this invention, the process of this invention will result in a compound of the general formula IV:

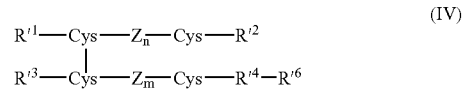

(IV)

wherein $Z_n$ and $Z_m$, independent of each other, represents two peptide moieties each containing n and m amino acid residues, respectively, $R'^1$ represents a peptide residue, $R'^2$ represents an amino acid residue or a peptide residue, $R'^3$ represents a peptide residue, $R'^4$ is as mentioned above, and $R'^6$ is an amino acid carrying a carboxy protecting group or a peptide residue, optionally carrying a carboxy protecting group.

Any carboxy protecting group (for example, $R^6$) and any hydroxy protecting group (for example, $R^5$) present in an insulin compounds can be removed by known methods or methods known per se. In case the carboxy protecting group is methyl, ethyl, or a group of the general formula —$CH_2$—$CH_2$—$SO_2R^7$, wherein $R^7$ is as defined above, said protecting group can be removed at gentle basic conditions in an aqueous medium, preferably at a pH value in the range from about 8 to about 12, for example, at about 9.5. As the base can be used strong bases, for example, a tertiary amine, for example triethylamine, hydroxides of alkali metals such as sodium hydroxide or hydroxides of alkaline earth metals such as calcium, or magnesium hydroxide. In case the carboxy protecting group is tert-butyl, substituted benzyl such as p-methoxybenzyl or 2,4,6-trimethylbenzyl, or diphenylmethyl, said group can be removed by acidolysis, preferably with trifluoroacetic acid. The trifluoroacetic acid may be nonaqueous or may contain some water, or it may be diluted with an organic solvent, such as dichloromethane. In case the hydroxy protecting group (for example, $R^5$) is tert-butyl, said group can be removed by acidolysis, vide above.

Preferably, the insulin compounds prepared have no hydroxy protecting group.

In a preferred embodiment of this invention, the process of this invention converts the insulin precursor (for example, of formula I) into an insulin compound (for example, formula IV), having a carboxy protecting group in the C terminal amino acid residue in the B chain which, then, can be deblocked to form an insulin compound having no carboxy protecting group.

When selecting the reaction conditions according to the above explanation and considering the results obtained in the following examples it is possible to obtain a yield of insulin compound which is higher than 60%, and even higher than 80%, and under certain preferred conditions higher than 90%.

By the process of this invention, insulin compounds of an acceptable purity can be obtained and be further purified, if desired, for therapeutic purpose.

More specifically, insulin aspart may, for example, be prepared by enzymatic cleavage with ALP of an insulin precursor such as [Asp$^{28}$]-des(30-65) human proinsulin being N-terminally extended with Glu-(Glu-Ala)$_3$-Pro-Lys- (SEQ ID NO.: 1) and coupling with a nucleophile compound such as L-threonine methyl ester, followed by hydrolysis.

Insulin lispro may, for example, be prepared by enzymatic cleavage with trypsin of a precursor such as porcine insulin and coupling with a nucleophile compound such as Gly-Phe-Phe-Tyr-Thr-Lys-Pro-Thr (SEQ ID NO.: 3).

Insulin glargin may, for example, be prepared by enzymatic cleavage with ALP of an insulin precursor such as [Gly$^{86}$]-des(30-65) human proinsulin and coupling with a nucleophile compound such as Thr-Arg-Arg-OMe, followed by hydrolysis.

Abbreviations used herein are in accordance with the rules approved (1974) by the IUPAC-IUB Commission on Biochemical Nomenclature, vide Collected Tentative Rules & Recommendations of the Commission on Biochemical Nomenclature IUPAC-IUB, 2$^{nd}$ edition, Maryland 1975.

The mentioning herein of a reference is no admission that it constitutes prior art.

Herein, the word "comprise" is to be interpreted broadly meaning "include", "contain" or "comprehend" (vide, the EPO guidelines C 4.13).

The following examples are offered by way of illustration, not by limitation.

EXAMPLE 1

200 mg [Ala$^{31}$,Lys$^{32}$]-des(33-63) porcine proinsulin was suspended in 1.35 ml water and the pH value was adjusted to 9 with 10 µl triethylamine. A mixture of 375 µl N,N-dimethylacetamide and 460 µl water was added with slightly agitation and to the resulting solution was added 315 µl of a 5.4 mg/ml aqueous solution of *Achromobacter lyticus* lysyl specific protease (EC 3.4 21.50) (herein designated ALP). The pH value was adjusted to 9.8 with 20 µl triethylamine and the reaction solution was left for 1 hour at 23° C. The reaction solution was acidified by addition of 70 µl 4 N hydrochloric acid and cooled in an ice bath. A solution of 300 mg L-threonine methyl ester in 4.85 ml N,N-dimethylacetamide was added and the pH value was adjusted to 6.5 by addition of 450 µl 4 N hydrochloric acid. The reaction solution was left for 4 hours at 23° C. after which the reaction was stopped by addition of hydrochloric acid to a pH value <3. By reversed phase HPLC analysis on a 4 mm×250 mm 5 µm C18 silica column with an ethanol-water eluent containing 0.125 M ammonium sulphate adjusted to a pH value 4, a conversion yield of 86% to human insulin methyl ester was found after a total reaction time of 5 hours.

For comparison, a one-step conversion was performed:

100 mg [Ala$^{31}$,Lys$^{32}$]-des(33-63) porcine proinsulin was suspended in a mixture of 887 µl water and 175 µl N,N-dimethylacetamide. 150 mg L-threonine methyl ester was dissolved in 2.265 ml N,N-dimethylacetamide and was slowly added to the ice-cooled mixture. The pH value was adjusted to 6.5 with 340 µl acetic acid and 158 µl, of a 5.4 mg/ml aqueous solution of ALP was added The conversion reaction was followed by RP-HPLC analysis of acidified samples. After 5 hours, a 53% conversion to human insulin methyl ester was found and after 24 hours the conversion reached a maximum of 87%.

The isolated human insulin methyl ester was converted into human insulin by dissolution in water at a pH value of 10 at a concentration of 10 mg/ml. The reaction was terminated after 24 hours by adjusting the pH value to 5.2 with 1 N hydrochloric acid and the precipitated human insulin was isolated by centrifugation and purified by reverse phase high performance liquid chromatography.

At the same reaction time, i.e, 5 hours, the yield by the process of this invention, compared with the per se known process, was improved with 62%. The two processes obtained almost the same yield, if the reaction time of the per se known one-step conversion was extended almost 5 times, compared with the reaction time for the process of this invention.

EXAMPLE 2

200 mg porcine insulin was suspended in 1.37 ml water and a mixture of 294 µl N-methyl-2-pyrrolidon and 326 µl water was added with slightly agitation. The pH value was adjusted to 9.0 with 10 µl 2 N sodium hydroxide and to the resulting solution was added 315 µl of a 5.4 mg/ml aqueous solution of ALP. The pH value was adjusted to 9.8 with 12 µl 2 N sodium hydroxide and the reaction solution was left for 4 hours at 23° C. The reaction solution was acidified by addition of 70 µl 4 N hydrochloric acid and cooled in an ice bath. A solution of 300 mg L-threonine methyl ester in 4.4 ml N-methyl-2-pyrrolidon was acidified with 500 µl 4 N hydrochloric acid. The insulin solution was slowly added and the pH value was adjusted to 6.5 with 50 µl 2 N hydrochloric acid. The reaction solution was left for 4 hours at 23° C. after which the reaction was stopped by addition of hydrochloric acid to a pH value<3. By reversed phase HPLC analysis on a 4 mm×250 mm 5 µm C18 silica column with an ethanol-water eluent containing 0.125 M ammonium sulphate adjusted to a pH value 4, a conversion yield of 86% to human insulin methyl ester was found after a total reaction time of 8 hours.

For comparison, a one-step conversion was performed:

100 mg porcine insulin was suspended in a mixture of 848 µl water and 147 µl N-methyl-2-pyrrolidon. 150 mg L-threonine methyl ester was dissolved in 2.2 ml N-methyl-2-pyrrolidon and was slowly added to the ice-cooled mixture. The pH value was adjusted to 6.5 with 300 µl acetic acid and 158 µl of a 5.4 mg/ml aqueous solution of ALP was added. The reaction solution was left at 23° C. and the conversion reaction was followed by RP-HPLC analysis of acidified samples. After 8 hours, the conversion was found to 54% and after 48 hours a conversion maximum of 86% to human insulin methyl ester was reached.

The isolated human insulin methyl ester can be converted to human insulin by alkaline hydrolysis.

At the same reaction time, i.e, 8 hours, the yield by the process of this invention was improved with 59%, compared with the per se known process. The two processes obtained the same yield, if the reaction time of the per se known one-step conversion was extended 6 times, compared with the reaction time for the process of this invention.

EXAMPLE 3

200 mg [Asp$^{28}$]-des(30-65) human proinsulin, N-terminally extended with the peptide Glu-(Glu-Ala)$_3$-Pro-Lys- (SEQ ID NO.: 1), was suspended in 1.35 ml water. A mixture of 350 µl N,N-dimethylformamide and 425 µl water was added with slightly agitation and the pH value was adjusted to 9 with 45 µl triethylamine. To the resulting solution was added 200 µl of a 8.5 mg/ml aqueous solution of ALP and the pH value was adjusted to 9.8 with 20 µl triethylamine. The reaction solution was left for 1 hour at 23° C. The reaction solution was acidified by addition of 70 µl 4 N hydrochloric acid and cooled in an ice bath. A solution of 300 mg L-threonine methyl ester in 4.95 ml N,N-dimethylformamide was added and the pH value was adjusted to 6.5 by addition of 470 µl 4 N hydrochloric acid. The reaction solution was left for 4 hours at 23° C. after which the reaction was stopped by addition of hydrochloric acid to a pH value <3. By reversed phase HPLC analysis on a 4 mm×250 mm 5 µl C18 silica column with an ethanol-water eluent containing 0.125 M ammonium sulphate adjusted to a pH value 4, a conversion yield of 87% to [Asp$^{B28}$]-human insulin methyl ester was found after a total reaction time of 5 hours.

For comparison, a one-step conversion was performed:

90 mg [Asp$^{28}$]-des(30-65) human proinsulin, N-terminally extended with the peptide Glu-(Glu-Ala)$_3$-Pro-Lys- (SEQ ID NO.: 1), was suspended in a mixture of 887 µl water and 175 µl N,N-dimethylformamide. 150 mg L-threonine methyl ester was dissolved in 2.13 ml N,N-dimethylformamide and was slowly added to the ice-cooled mixture. The pH value was adjusted to 6.5 with 250 µl acetic acid and 118 µl of a 8.5 mg/ml aqueous solution of ALP was added. The conversion reaction was followed by RP-HPLC analysis of acidified samples. After 5 hours, the conversion was found to 47% and after 24 hours the conversion to [Asp$^{B28}$]-human insulin methyl ester reached a maximum of 81%.

The isolated insulin methyl ester can be converted to [Asp$^{B28}$]-human insulin by alkaline hydrolysis.

At the same reaction time, i e., 5 hours, the yield by the process of this invention was almost doubled, compared with the per se known process. Comparable yields ware obtained by the two processes, if the reaction time of the per se known one-step conversion was extended nearly 5 times, compared with the reaction time for the process of this invention.

EXAMPLE 4

1.5 g insulin aspart precursor [Asp$^{28}$,Met$^{30}$,Trp$^{31}$,Lys$^{32}$]-des(33-65) human proinsulin, N-terminally extended with the peptide Glu-Glu-Gly-Glu-Pro-Lys- (SEQ ID NO.: 2) was suspended in 3.5 g water. With slight agitation and at ambient temperature, the precursor was dissolved by gradually adding 4M sodium hydroxide to a pH value of 10.67. 3.7 g of a 45% (weight/weight) solution of ethanol in water was added. 1.5 ml of a 5.8 mg/ml aqueous solution of ALP was added and the mixture was left to react for 2 hours. The pH value was adjusted to 4.7 by addition of 4 N hydrochloric acid. 2.025 g L-threonine ethyl ester was dissolved in 16.2 ml ethanol and the solution was added at a maximum temperature of 15° C. The pH value was adjusted to 6.5 with 4 N hydrochloric acid. The temperature was adjusted to ambient temperature and the reaction mixture was left for 20 hours at this temperature. By reversed phase HPLC analysis on a 4 mm×250 mm 5 µm C18 silica column with an acetonitrile-water eluent containing 200 mM sodium sulphate adjusted to a pH value of 3.6, a conversion yield of 89.1% insulin aspart ethyl ester was found after 1 hours reaction time and after 20 hours reaction time, a conversion yield of 90.5% was found.

The isolated insulin aspart ethyl ester can be converted to insulin aspart by alkaline hydrolysis.

EXAMPLE 5

10 9 g insulin aspart precursor [Asp$^{28}$,Met$^{30}$,Trp$^{31}$,Lys$^{32}$]-des(33-65) human proinsulin, N-terminally extended with the peptide Glu-Glu-Gly-Glu-Pro-Lys- (SEQ ID NO.: 2) was suspended in 49.3 g water. With slight agitation and at ambient temperature, the precursor was dissolved by gradually adding 37.6 g from a mixture containing 0.36 M sodium hydroxide, 0.27 M sodium acetate and 36% N-methyl-2-pyrrolidon. The pH value was adjusted to 9.7 with 9.2 ml 0.5 M sodium hydroxide. 7.1 mL of a 7.1 mg/mL aqueous solution of ALP was added, and the mixture was left to react for 5 hours. The pH value was kept constant at 9.7 by adding more 0.5 M sodium hydroxide throughout the reaction. The reaction mixture was cooled to 5° C. and the pH value was adjusted to 5.7 by addition of 2.73 g 4 N hydrochloric acid. 14.02 g L-threonine ethyl ester was added and the pH value was adjusted to 6.0 with 4 N hydrochloric acid. 344 g cold (4° C.) N-methyl-2-pyrrolidon was added. The temperature was adjusted to 22° C. and the pH value adjusted to 6.5 with 4 N hydrochloric acid. The reaction mixture was left for 9 hours at this temperature. By reversed phase HPLC analysis on a 4 mm×250 mm 5 µm C18 silica column with an acetonitrile-water eluent containing 200 mM sodium sulphate adjusted to a pH value of 3.6, a conversion yield of 87.5% to insulin aspart ethyl ester was found after a total reaction time of 14 hours.

The isolated insulin aspart ethyl ester can be converted to insulin aspart by alkaline hydrolysis.

The invention claimed is:

1. A process for preparing an insulin compound, said process comprising two steps, a first cleavage step and a second coupling step, wherein said cleavage step comprises: reacting an insulin precursor with an enzyme in a reaction mixture containing at least about 55% water (weight/weight) to produce an intermediate cleavage product; and said coupling step comprises: adding a nucleophile compound to the intermediate cleavage product of said coupling step in a reaction mixture having a content of water from about 10% to about 50% water (weight/weight), and reacting said intermediate cleavage product with said nucleophile compound to produce said insulin compound, wherein said nucleophile compound is selected from the group consisting of: an amino acid ester and an amino acid amide.

2. The process, according to claim 1, wherein the enzyme used in said first cleavage step is present in said second coupling step.

3. The process according to claim 1, wherein at least about 25% of the insulin precursor is cleaved to the intermediate cleavage product in said first cleavage step.

4. The process according to claim 1, wherein at least about 50% of the insulin precursor is cleaved to the intermediate cleavage product in said first cleavage step.

5. The process according to claim 1, wherein at least about 75% of the insulin precursor is cleaved to the intermediate cleavage product in said first cleavage step.

6. The process according to claim 1, wherein at least about 85% of the insulin precursor is cleaved to the intermediate cleavage product in said first cleavage step.

7. The process according to claim 1, wherein at least about 95% of the insulin precursor is cleaved to the intermediate cleavage product in said first cleavage step.

8. The process according to claim 1, wherein the enzyme used in said first cleavage step is trypsin or a lysyl specific protease.

9. The process according to claim 8, wherein the enzyme is *Achromobacter lyticus* protease I.

10. The process according to claim 1, wherein the amino acid ester is a threonine ester.

11. The process according to claim 1, wherein the insulin compound produced in said second coupling step has a carboxy and/or hydroxy protecting group.

12. The process according to claim 11, wherein said process further includes as a third step of removing the protecting group(s) from the insulin compound produced in said second coupling step.

13. The process according to claim 1, wherein the insulin compound produced in said second coupling step has threonine in the B30 position.

14. The process according to claim 1, wherein the insulin compound produced in said second coupling step is human insulin, insulin aspart, insulin lispro, insulin glargine, or insulin detemir.

15. The process according to claim 1, wherein the reaction mixture in said first cleavage step contains at least about 60% water (weight/weight).

16. The process according to claim 1, wherein the reaction mixture in said first cleavage step contains at least about 70% water (weight/weight).

17. The process according to claim 15, wherein the content of water in the reaction mixture of said second coupling step is from about 20 to about 40% water (weight/weight).

18. The process according to claim 16, wherein the content of water in the reaction mixture of said second coupling step is from about 20 to about 40% water (weight/weight).

19. The process according to claim 1, wherein the nucleophile compound and the intermediate product in said second coupling step are present in a molar ratio of greater than 5:1.

20. The process according to claim 19, wherein the molar ratio of nucleophile compound to intermediate product is greater than 50:1.

21. The process according to claim 1, wherein the content of water in the reaction mixture of said second coupling step is from about 20 to about 40% water (weight/weight).

22. The process according to claim 1, wherein the concentration of the insulin precursor in the reaction mixture of said first cleavage step is from about 5% to about 10% (weight/vol).

23. The process according to claim 1, wherein the amount of enzyme as compared to the amount of insulin precursor in said first cleavage step is in a range from about 0.5% to about 5% (weight/weight).

24. The process according to claim 1, wherein the reaction mixture in said first cleavage step has a pH of from about 6 to about 11.

25. A process for preparing an insulin compound, said process comprising two steps, a first cleavage step and a second coupling step, wherein said cleavage step comprises: reacting an insulin precursor with an enzyme in a reaction mixture containing at least about 55% water (weight/weight) to produce an intermediate cleavage product; and said coupling step comprises: adding a nucleophile compound to the intermediate cleavage product of said coupling step in a reaction mixture having a content of water from about 10% to about 50% water (weight/weight), and reacting said intermediate cleavage product with said nucleophile compound to produce said insulin compound, wherein said nucleophile compound is selected from the group consisting of: an amino acid ester and an amino acid amide and wherein the intermediate cleavage product produced in said first cleavage step is not isolated prior to said second coupling step.

26. The process according to claim 25, wherein at least about 25% of the insulin precursor is cleaved to the intermediate cleavage product in said first cleavage step.

27. The process according to claim 25, wherein at least about 50% of the insulin precursor is cleaved to the intermediate cleavage product in said first cleavage step.

28. The process according to claim 25, wherein at least about 75% of the insulin precursor is cleaved to the intermediate cleavage product in said first cleavage step.

29. The process according to claim 25, wherein at least about 85% of the insulin precursor is cleaved to the intermediate cleavage product in said first cleavage step.

30. The process according to claim 25, wherein at least about 95% of the insulin precursor is cleaved to the intermediate cleavage product in said first cleavage step.

31. The process according to claim 25, wherein the enzyme used in said first cleavage step is trypsin or a lysyl specific protease.

32. The process according to claim 31, wherein the enzyme is *Achromobacter lyticus* protease I.

33. The process according to claim 25, wherein the amino acid ester is a threonine ester.

34. The process according to claim 25, wherein the insulin compound produced in said second coupling step has a carboxy and/or hydroxy protecting group.

35. The process according to claim 34, wherein said process further includes as a third step of removing the protecting group(s) from the insulin compound produced in said second coupling step.

36. The process according to claim 25, wherein the insulin compound produced in said second coupling step has threonine in the B30 position.

37. The process according to claim 25, wherein the insulin compound produced in said second coupling step is human insulin, insulin aspart, insulin lispro, insulin glargine, or insulin detemir.

38. The process according to claim 25, wherein the reaction mixture in said first cleavage step contains at least about 60% water (weight/weight).

39. The process according to claim 25, wherein the reaction mixture in said first cleavage step contains at least about 70% water (weight/weight).

40. The process according to claim 25, wherein the content of water in the reaction mixture of said second coupling step is from about 20 to about 40% water (weight/weight).

41. The process according to claim 25, wherein the nucleophile compound and the intermediate product in said second coupling step are present in a molar ratio of greater than 5:1.

42. The process according to claim 41, wherein the molar ratio of nucleophile compound to intermediate product is greater than 50:1.

43. The process according to claim 25, wherein the concentration of the insulin precursor in the reaction mixture of said first cleavage step is from about 5% to about 10% (weight/vol).

44. The process according to claim 25, wherein the amount of enzyme as compared to the amount of insulin precursor in said first cleavage step is in a range from about 0.5% to about 5% (weight/weight).

45. The process according to claim 25, wherein the reaction mixture in said first cleavage step has a pH of from about 6 to about 11.

* * * * *